(12) United States Patent
Bruun-Jensen

(10) Patent No.: US 6,382,408 B1
(45) Date of Patent: May 7, 2002

(54) CONTAINER FOR TIMED RELEASE OF SUBSTANCES

(75) Inventor: Jorgen Bruun-Jensen, Slagelse (DK)

(73) Assignee: Synoptik A/S, Rodovre (DK)

( * ) Notice: Subject to any disclaimer, the term of this patent is extended or adjusted under 35 U.S.C. 154(b) by 0 days.

(21) Appl. No.: 09/581,136

(22) PCT Filed: Dec. 14, 1998

(86) PCT No.: PCT/DK98/00551

§ 371 Date: Aug. 9, 2000

§ 102(e) Date: Aug. 9, 2000

(87) PCT Pub. No.: WO99/30746

PCT Pub. Date: Jun. 24, 1999

(30) Foreign Application Priority Data

Dec. 12, 1997 (DK) .......................................... 1997 1446

(51) Int. Cl.$^7$ ................................................ A45C 11/04
(52) U.S. Cl. ...................... 206/5.1; 134/901; 422/301
(58) Field of Search ........................ 206/5.1; 134/137, 134/901; 422/301

(56) References Cited

U.S. PATENT DOCUMENTS

| | | | |
|---|---|---|---|
| 3,394,717 A | 7/1968 | Hollinger | 134/137 |
| 5,186,317 A | 2/1993 | Ryder et al. | 206/5.1 |
| 5,306,352 A | 4/1994 | Nicolson et al. | 134/42 |
| 5,364,601 A | 11/1994 | Salpekar | 422/28 |
| 5,381,091 A | 1/1995 | Rontome et al. | 422/30 |
| 5,468,448 A | 11/1995 | Nicolson et al. | 422/30 |

FOREIGN PATENT DOCUMENTS

| | | |
|---|---|---|
| EP | 384 642 B1 | 8/1990 |
| EP | 486 653 B1 | 5/1992 |
| EP | 514 311 B1 | 11/1992 |
| EP | 560 728 A1 | 9/1993 |
| EP | 574 353 A1 | 12/1993 |
| EP | 739 598 A1 | 10/1996 |
| FR | 2 638 248 | 4/1990 |
| FR | 2 658 422 | 8/1991 |
| GB | 2 151 039 | 7/1985 |
| GB | 2 301 198 | 11/1996 |
| WO | 90/11786 | 10/1990 |
| WO | 94/01800 | 1/1994 |
| WO | 94/16743 | 8/1994 |
| WO | 95/12141 | 5/1995 |
| WO | 96/40081 | 12/1996 |

*Primary Examiner*—David T. Fidei
(74) *Attorney, Agent, or Firm*—Foley & Lardner

(57) ABSTRACT

A container suitable for holding at least one substance for use in a process for cleaning contact lenses using a fluid, includes at least one first and at least one second part assembled to form a sealed cavity for holding the substance, the first and the second parts being formed of a material having an expansion coefficient when embedded in the fluid. The dimensioning of the first and the second parts and the expansion coefficients are chosen so that, subsequent to the expansion of the first and/or the second parts, an opening is defined between the first and the second parts.

66 Claims, 7 Drawing Sheets

CONTAINER FOR TIMED RELEASE OF SUBSTANCES

BACKGROUND OF THE INVENTION

1. Field of the Invention

The present invention relates to the art of for cleaning contact lenses and in a specific embodiment to apparatus for performing a multi-step cleansing of contact lenses where, during a first step, cleansing is performed using a high and substantially constant concentration of the cleansing agent or agents in the cleansing fluid and where, during a second, subsequent step, the cleansing agent or agents are neutralized and/or the cleansing fluid is altered in order to make the cleansed contact lenses more suitable for insertion onto a users eyes.

2. Description of the Related Art

A high concentration of the cleaning substance in the cleaning fluid is required, because some of the impurities usually deposited on the lenses require a long exposure time to a disinfection fluid, e.g. hydrogen peroxide with a concentration of 3–4 vol. %, in order to be removed. Examples of such impurities are acanthameoba, candida albicans, yeast cells, different vira and different bacteria spores. These impurities are known to be very resistant to commonly used disinfection fluids, so in order to remove such impurities, a long exposure time is required with a high concentration of the active substance in the disinfection or cleansing fluid.

Furthermore, e.g. bacteria can excrete chemical/biological substances which can encapsulate the bacteria, i.e. form a film of chemical/biological substances which adhere to the surface of a contact lens. Thus, a long exposure time is also required in order for the disinfection or cleansing fluid to penetrate and thereby remove the bacteria and bacteria spores and the film of chemical/biological substances.

In fact, most of the presently known apparatus and methods may be denoted as bacteriostatic in that the interaction with the cleansing fluid is only sufficient for maintaining a level of bacterial contamination in the container used for holding the contact leans during cleansing.

Known apparatus for cleansing contact lenses are typically ones in which the contact lens and the cleansing fluid are introduced into a container. However, in order to avoid requiring that the user himself has to introduce an agent for neutralizing the cleansing fluid (in order to render the contact lens suitable for introduction onto the users eye), this neutralizing agent is introduced from the beginning of the process. Consequently, the neutralization of the cleansing fluid takes place during the full process, whereby the concentration of the cleansing agent is only optimum for a short period of time. Naturally, this requires a longer period of time for a suitable cleansing of the contact lens.

Apparatus which attempt to postpone the active neutralization process of the disinfection fluid are known from EP 2 658 422. In this apparatus the neutralizing agent is placed in the container wherein the disinfection process takes place by means of a mechanical device. This mechanical device can be driven by an electric motor or it can be driven manually.

Another apparatus which attempts to postpone the relief of a neutralising agent is known from GB 2 301 1 98 A. In this apparatus the neutralising agent is kept in a cavity defined by a tubular part being open ended in one end only. The cavity is sealed by a lid settled inside the tubular part, which lid swells when in contact with a disinfecting fluid. As the lid is settled inside the tubular part, a cavity, defined by side parts of the tubular part and the lid, is present on top of the lid. Due to the small dimension of the apparatus and the surface tension in the disinfecting fluid, air bubbles will tend to deposit in this cavity in use. If an air bubble deposits in the cavity, access to the surface of the lid is hindered and the swelling process will not take place, whereby no access for the cleaning fluid to the neutralising agent is provided and the neutralisation process does not take place. Furthermore, the introduction of the apparatus into a receptacle used for the cleaning process is critical in the sense that no swelling of the lid will occur, if the apparatus "lands" standing on its open end, due to the fact that no fluid or not a sufficient amount of the fluid will be able to get into contact with the lid.

Other manners of delaying the introduction of the neutralizing agent would be using the well known sustained release principle where the agent is formed into a pill or pellet covered by a layer dissolved by the cleansing agent. In this manner, the neutralizing agent is not released until the layer has been dissolved. This method, however, has the disadvantage that the material of the layer and e.g. pill manufacturing helping agents will be released to the cleansing agent, part of which will be introduced onto the eye of the user or will remain in the container means used for the cleansing. These materials are typically of a type that attracts and holds bacteria and, consequently, facilitates bacterial growth in the container means and hence on the contact lenses.

BRIEF SUMMARY OF THE INVENTION

Thus, it is an object of the invention to provide a container means for use in cleansing a contact lens, which firstly is able to reduce or fully obviate the introduction of unsuitable agents (mostly agents irritating to the eye) in the cleansing fluid, and which secondly is adapted to fully delay the neutralization of the cleansing agent until after a desired period of time where the contact lens has been sufficiently cleansed. Both these objects will help to reduce the bacterial growth in the container used for the cleansing and thereby the concentration of bacterial present on the cleansed contact lens. Thus, the present method will facilitate bactericide cleansing—that is, a cleansing actually reducing the number of bacteria in the container and, thus, on the cleansed contact lens.

These objects are obtained by a container means suitable for holding at least one substance for use in a process for cleaning contact lenses using a fluid, the container means comprising:

- at least one first and at least one second part assembled/combined to form a sealed cavity for holding the at least one substance,
- the second part(s) being formed of a material having a second expansion coefficient when embedded in the fluid and being at least substantially insoluble in the fluid, the second part(s) having outer surface(s) constituting part(s) of an outer surface of the container means,
- the first part(s) being formed of a material having a first expansion coefficient when embedded in the fluid and being at least substantially insoluble in the fluid, the first expansion coefficient being smaller than the second expansion coefficient, wherein
 the container means has at least one cross section wherein the first part(s) define(s) an envelope curve and wherein at least one part of the second part(s) extend(s) outside the envelope surface,
and/or
two or more parts of the outer surface of the assembled/combined container means are constituted by surface parts of the second part(s) at at least two different sides thereof.

It should be noted that, in the present context, an expansion coefficient may be negative so that the material, in fact, shrinks when in contact with the fluid.

In the following, the invention will be described where one of the materials expands more than the other. It should be noted that exactly the same effect will be achieved if the other material shrinks correspondingly in relation to the first material.

The material being able to expand should be at least substantially insoluble in the so as to avoid polution of the fluid used in the process for cleaning contact lenses. Polution may e.g. be the case where the material is no longer interconnected so that the material is able to deposit on the lenses. It is preferred that the fraction of the material no longer being interconnected should be less than 5%, preferably less than 4%, such as less than 3%, preferably less than 2%, such as less than 1%, preferably less than 0.5, even less than 0.25% and preferably less than 0.125%, the amount being measured in mass fraction.

In the following context, the envelope curve is a curve where all concavities are replaced by straight lines so that only convexities and straight lines remain.

One advantage obtained by part of the second part extending outside the envelope curve of the first parts is that should the container means "land" on a surface in the area where the cavities of the first part(s) are, the part(s) of the second parts will extend beyond these parts, whereby the fluid will gain access to these part(s) of the second parts. If the first part(s) and a bubble or a receptacle holding the container means, the fluid etc. were to be able to fully enclose the outer surface of the first part(s), no release of the substance would take place. Thus, this feature of the invention will act to enhance the chance of the release of the substance taking place.

Also, when the part(s) of the second part(s) extends outside the envelope, it will be less probable for a bubble to cover all of the extending part(s), whereby also this effect is made much more improbable.

In this context, the fact that parts of different sides of the outer surface of the container means are constituted by parts of the second part(s) means that should the container means "land" on one of those sides, the other side will not be blocked by the contact between the container means and a receptacle holding the container means, the fluid etc.

More specifically, two different sides would typically be different parts of the container means as seen from two directions at an angle of at least 20 degrees, preferably at least 30 degrees, such as at least 45 degrees, preferably at least 60 degrees, such as at least 90 degrees, preferably on the order of 180 degrees.

An advantage obtained by this feature is the fact that, should one side be blocked either by a bubble or by the container means "landing" on that side, the other side would typically be exposed to the fluid, whereby the release of the substance will not be hampered.

The fluid used may simply be water and the substance a disinfecting or cleansing agent, such as an enzyme, or the fluid may itself be a disinfecting or cleansing fluid and the substance a neutralising agent. Common to the process or holding means is the fact that the access to the substance is delayed in order to divide the cleansing process into two distinctly different phases—one with and one without the interaction of the substance.

In a preferred embodiment, the first part defines an open cavity and the second part defines a cover at least substantially closing the cavity of the first part.

In this embodiment, the second part may abut the first part along an inner or an outer surface part thereof, at least part of the inner or outer surface part of the first part being at an angle to the predetermined direction. In this manner, the difference of expansion will generate access to the substance, as two parts of the first and second parts, respectively, abutting in the unexpanded state of the holding means, will not expand to the same degree, whereby the abutment will be removed and, consequently, an opening be generated.

Alternatively or additionally, the second part may abut the first part along an end surface part thereof, the end surface part typically corresponding to e.g. the upper edge of a cup or similar container.

In this situation, the difference in expansion will not automatically generate access to the substance, as the expansion of two abutting parts (as above) will be in substantially the same direction. Therefore, the difference in expansion should be large enough for the abutting surface parts of the first and second parts to disengage and thereby form access to the substance in the holding means. In other words, the dimensioning of the first and second parts and the first and second expansion coefficients are preferably chosen so that, subsequent to the expansion of the first and/or second parts, an opening is defined between the first and second parts and at the at least part of the end surface part. Thus, if the abutting surface parts form eg a circle, the difference in expansion is preferably larger than the largest thickness of the abutting surface parts in order to ensure that a gap is formed.

In the preferred embodiment, the second part preferably has a tubular part, an outer edge portion of which is to be exposed to the fluid. This tubular part has an advantage when the expansion of the first and/or second parts is e.g. a swelling. The swelling of a tubular part is an overall increase in the diameter or dimensions of the tubular part. When the outer edge portion is to be exposed to the fluid, the expansion will be quickest at this edge portion so that the expansion of the tubular part will be a funnel-shaped deformation due to the expansion along the full circumference pressing the expanded material outwards.

In another embodiment, the first part defines a plurality of open cavities, the second part defining a cover at least substantially closing the cavities of the first part.

As will be clear from the following, this funnel-shaped deformation may also be used for timing the release of several substances in the fluid.

It may be preferred that the first part defines a plurality of open cavities, the second part defining a cover at least substantially closing the cavities of the first part. In this situation, it may be desired that access to substances present in the individual cavities is timed differently.

One manner of obtaining this timing is one wherein the plurality of open cavities are positioned at least substantially concentrically and are separated by separating walls of the first part. Naturally, these cavities need not be circular.

In this situation, the tubular part preferably encircles an outer cavity of the open cavities in order to take advantage of the above-mentioned funnel-shaped deformation.

Preferably, the first and second parts are biased towards each other. As those first parts of the second part which firstly deform and expand will typically be the outer parts thereof, these will not be suitable for providing this biasing: they would quickly release the closure and thereby provide access to the contents of all cavities in the first element. Therefore, this biassing may be obtained by biassing the separating walls of the first part toward internal biassing means of the second part, the separating walls and/or the biassing means closing, at least in an unexpanded state, one of the cavities of the first part. This closure may be obtained by the closing action of the first part being kept in place by the biassing. In this manner, the access to contents of this one cavity will be prevented at the point in time where access is obtained to the outer cavity.

In that situation, the thickness of the biassing means and/or especially the part of the second part defining the closure of the at least one of the cavities may be adapted so that the opening of this cavity takes place a predetermined time after contacting the holding means and the fluid or after the point in time where the fluid gained access the outer cavities.

Another manner of providing a plurality of cavities is aligning these side by side in the first part, the open cavities being separated by separating walls. In this situation, the tubular part is preferably positioned so as to have an axis of symmetry along the aligned open cavities.

The funnel-shaped deformation of the tubular part naturally depends on the manner in which the expansion takes place along the circumference of the tubular part. Preferably, the outer edge portion is positioned at least substantially within a plane, such as within a few times the thickness of the material of the first or second parts at that position, in order to ensure that the expansion of the material in fact provides the funnel-shaped deformation.

As described above, the funnel-shaped deformation is generated by the outer parts of the tubular part expanding more quickly than the more central parts thereof. As this deformation has the above advantages, it is preferred that, at the outer edge portion, the second part has, compared to a main part of the second part, a larger proportion of the part of the surface thereof to be exposed to the fluid in relation to the volume of the material. This may be provided by increasing the surface to be exposed to the fluid but also by reducing e.g. the thickness of the material of the second element compared to the thickness at other parts of the second part.

Thus, by selecting the thickness of the material of the second part, timing of the release of the individual substances may be selected, such as in a way that e.g. only a short time is needed for getting access to a first closed cavity due and e.g. a relatively longer time period is needed to gain access to a second closed cavity. In such a case, thickness of the second part that is closing the first cavity would be substantially thinner than the part closing the second cavity.

As described above, it is preferred that the first and the second part are biased toward each other.

For example, the first and the second parts may be shaped so as to be combined without the use of any separate fixing or combining means.

Alternatively, two parts actually defining the cavity may be provided and assembled using a separate fixing means, such as a fixing means holding the two parts in place, the fixing means having a coefficient of expansion larger than the two elements so that the fixing means will, at a point in time, release the two parts so that these may separate and release the substance held thereby.

The lack of glue or other additional substances has e.g. the advantage that no additional substances, such as glue etc, are required in order to hold the two parts in place during the first part of the cleansing process. These additional substances might not be desired in the cleansing fluid, as part of this might adhere to the contact lens when introduced onto the eye of the user.

The above embodiment has been described as one where the first part defines a cavity and the second part closes the cavity. Naturally the same advantages and effect may obtained when the second part defines a cavity and the first closes the cavity.

The first expansion coefficient may be one where a sheet of the material of the first part having a thickness of 1 mm in an unexpanded condition will expand to a mean thickness of 0.5–10 mm, such as a thickness of 0.7–1.5 mm, preferably a thickness of 1 mm, when fully expanded in the fluid.

The second expansion coefficient may be one where a sheet of the material of the second part having a thickness of 1 mm in an unexpanded condition will expand to a mean thickness of 1–10 mm, such as a thickness of 1.2–5 mm, preferably a thickness of 1.4–2 mm, when fully expanded in the fluid.

However, such materials can have an even larger expansion once the substance has been released into the fluid. The presently preferred material has an expansion of the order of 200% in the $H_2O_2$ but on the order of more than 500% in pure water which would results from an neutralisation of the $H_2O_2$ with catalase.

Preferably, the second expansion coefficient is larger than the first expansion coefficient, and the materials of the first and second parts are preferably so that an initial, unexpanded sheet of the material of the second part and of a predetermined thickness will expand to a sheet of a mean thickness of at least 105%, such as at least 110%, such as about at least 140% of the mean thickness of a fully expanded sheet of the material of the first material and of the same initial unexpanded predetermined thickness.

Especially in embodiments where the part having the largest expansion is positioned more or less within the other part, it may be preferred that the first part is provided with means for facilitating deformation or breaking thereof at one or more predetermined points or along one or more predetermined lines in order for the expansion of the expanding part to be able to provide the access to the substance by simply breaking or deforming the other part.

Also, in this context, it should be noted that the "expansion" of one of the elements in relation to the other may as well be a shrinking of the other element in relation to the first element. In order to provide the access of the fluid to the substance, only a difference in change of dimension is required.

As described above, a major problem of the prior art is the action of bubbles blocking the access of the fluid to the expanding material or that the relatively non-expanding material is able together with the receptacle is able to block this access.

This adverse effect may be removed where the at least one part of the second part(s) extending outside the envelope surface has a part being convex. In this manner, if the extending part actually forms a convex part of the outer surface of the container means, this convexity may prevent the container means from actually "landing" on this side. Also, bubbles are less probable to form on such convex surfaces.

In order to further improve the probability of the container means actually being oriented in the fluid in the optimum manner, the container means may further comprise orientation means for orientation of the container means relative to the horizontal direction when positioned in a receptacle, the receptacle being adapted to hold the container means, the contact lenses, and the fluid when the contact lenses are cleaned.

In this manner, the orientation means may be adapted to hold the container means with its axis of symmetry being substantially horizontal.

Also, having introduced this "additional" element, it may be used also for other purposes. Thus, it may further comprise enclosing means for enclosing the container means. As described above, the expanding material may have a total degree of expansion to a degree where it is quite large and may interact, when the user retrieves the contact lenses. Also, if the shape of the expanded material should look like a contact lens, it would be desirable to "separate" it from the lenses in order to prevent the user from introducing the wrong element onto his/her eye.

Therefore, the enclosing means may comprise a porous or liquid penetrable means being adapted to allow the fluid to travel into the enclosing means and to prevent at least a major part of the expanded second part(s) from escaping the enclosing means.

In addition, the orientation means may further comprise means for holding the contact lenses during cleansing thereof.

As described above, the shape and dimensions of the container means has a large say in how and where bubbles form and how the container means can "land" in the receptacle.

In a presently preferred embodiment, the container means is flat in a given direction when compared with the extension thereof in the two directions perpendicular thereto and to each other.

This is especially easy to see, when combined with the directing means, as these dimensions may now firstly ensure that the "lid" of expandable material actually gains access to the fluid, that it actually expands, that it actually provides sufficient access to the substance so that the interaction between the substance and the fluid actually takes place.

Yet another problem in this type of container means for providing a timed release of a substance in a fluid will be seen when the interaction between the fluid and the substance generates e.g. a gas. As will be clear, the expansion of the expandable material may not fully remove this from the substance or provide a large gap for the fluid to enter through—and the gas to escape through. In this situation, the access of the fluid to the substance may generate an increased pressure at the substance so that the expanded material is removed further—an advantageous effect. However, it may otherwise generate a gas bubble that will not escape through the gap but actually block the gap—and thereby stop the process even though the material has had sufficient access to the fluid and is fully expanded.

In this specific embodiment, the container means is positioned with the given direction along a horizontal direction.

Preferably, the extension of the container means along the given direction is at least 2, such as 3, preferably 4, such as about 5, such as at least 6, preferably 10, such as 20, such as about 30, preferably 50, such as 70, preferably 85 such as 100 times smaller than the extension of the container means along any of the two directions.

Also, it is advantageous that the extension of the container means in the given direction is less than 2 mm, such as less than 1.5 mm, preferably 1 mm, such as about 0.75 mm such as at least 0.5 mm and even less than 0.3 mm.

Especially where:

the first part(s) define a cavity having a bottom part and side parts and wherein the second part(s) in the assembled/combined container means close the cavity of the first part(s), an internal height of the side parts from an internal surface part of the bottom part is less than 2 mm, such as less than 1.5 mm, preferably 1 mm, such as about 0.75 mm such as at least 0.5 and even less than 0.2 mm, and where the second part(s) define a cavity, the cavity having a depth in the direction of the axis of symmetry, not exceeding 2 mm, such as not exceeding 1.5 mm, preferably not exceeding 1 mm, such as about not exceeding 0.5 mm, and even not exceeding 0.1 mm, it will be seen that the expanded second part(s) will easily disengage from the first part(s) and due to the interaction of gravity be fully removed from the cavity of the first part(s) holding the substance.

Also preferred is it when the container means has an axis of symmetry directed at least substantially along the direction of the height of the side parts of the second part(s).

From the above dimensions it may be seen that the height of the side parts are not able to hold a bubble, whereby that "trap" is avoided. However, it is also preferred that the first part is not able to trap a bubble. Therefore, it is preferred that the second part(s) define a cavity, the cavity having a depth in the direction of the axis of symmetry, not exceeding 2 mm, such as not exceeding 1.5 mm, preferably not exceeding 1 mm, such as about not exceeding 0.5 mm, and even not exceeding 0.1 mm. Dimensions that small will under usual conditions not hold a bubble large enough to stop the process.

An additional manner of ensuring that the process will take place is to ensure that and the substance will be able to fully remove itself therefrom when the expanded material is fully expanded. One manner of obtaining this is to have the second part(s) define a cavity, the cavity being shaped so that, when the axis of symmetry is at least substantially horizontal, no part of the inner surface of the cavity is horizontal. Thus, the substance positioned within the cavity will fall from this cavity, when the container means is oriented in the preferred manner.

Even though the "expansion" due to the contact of the fluid may be caused by a number of effects, such as due to a pH value of the fluid or a concentration of one or more salts—or even the temperature of the fluid, it is preferred that at least one of the first or second parts is of a material swelling when in contact with the fluid. This swelling firstly takes part at the surface parts contacted by the fluid and firstly later the fluid enters the inner parts of the material and then expands these portions. This will provide the above-mentioned funnel-shaped deformation as an intermediate state and a final, fully expanded state of the material. Furthermore, the swelling is an effect where the swelling material simply expands but does not release, generate or emit any particles or substances, it does not react with the fluid in a manner so that additional substances are formed, whereby the above-mentioned advantages also relating to the lack of glue etc. in the combining or assembling of the container means are obtained.

In fact, a material, such as polyhema, normally used for contact lenses actually expands (polyhema expands about 40%) when in contact with water, and materials (not expanding in water) typically used for containers for holding or cleansing contact lenses may be used in the present container means. The advantage of this is that these materials have already been accepted for use in connection with contact lens cleansing so that no side effects can take place.

Another advantage of the invention is that a cleansing system may be provided which can facility cleaning of contact lenses using different cleansing agents which can not coexist. This is possible because the release of the cleansing agents can be timed so that e.g. after a cleansing process using one agent, another agent can be released.

Another possibility is the case where $H_2O_2$ with a pH-value of 3–3.5 is utilized as the disinfection fluid (in order to get a bactericide cleansing of the lenses), a release of an agent that can alter the pH-value of the cleansing fluid at the end of the cleaning process to a value that is comfortable to the user when introducing the contact lens onto the eye. This altering or neutralizing agent may be catalase. Also, at the same time, before or after, a salt may be released into the fluid in order to bring about a physiological salt concentration also more pleasant for the user of the contact lens.

In addition, the use of different enzymes, which are not able to coexist or which function better when not coexisting, may be facilitated by the presently provided different timing between the release of different substances in the fluid.

The actual timing of the release or different releases may depend on the wishes of the user or the demands of the cleansing process. Different holding means may be provided for eg long term (or optimal) cleansing and shorter term (and thus less optimal) cleansing. A long term cleansing may be one taking place over night—such as where the substance or at least one of the substances is/are not released before after 2 hours, such as after 4 hours, such as after 6 hours. A short term cleansing may be one where the or a substance is released after no more than 2 hours, such as no more than 1 hour, such as no more than ½ hour.

In the situation where the last substance to be released is one actually stopping the cleansing process, this would be that described above. Other substances may, however, be released before in the process of—or actually starting—the cleansing process.

BRIEF DESCRIPTION OF THE DRAWINGS

In the following, the invention will be described by way of examples illustrating preferred embodiments thereof and with reference to the drawings wherein.

DETAILED DESCRIPTION OF THE PREFERRED EMBODIMENTS

In the following it is assumed that hydrogen peroxide is utilized as the disinfection fluid and that (enzyme) catalase is utilized as a neutralizing agent. Many other choices of cleaning components are of course possible, but in order to ease the description of the invention the combination of hydrogen peroxide and catalase is used in the examples.

Figure 1:
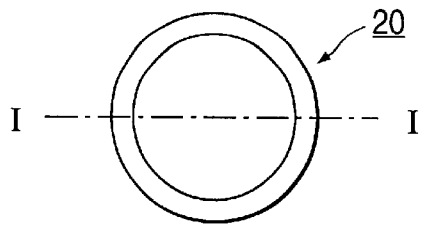
FIG. 1 is a top view of a container means in a first embodiment of the invention.
Figure 2:
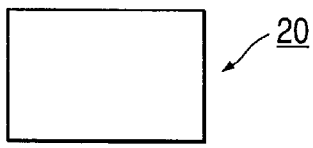
FIG. 2 is a side view of the container means of FIG. 1 in the first embodiment of the invention.
Figure 3:
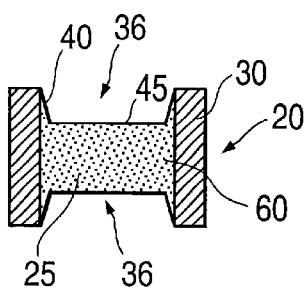
FIG. 3 is a cross-sectional view of the container means of FIG. 1 along line I—I, in the first embodiment in the invention.

Referring to FIGS. 1–3, a container means 20 used for holding the neutralizing agent 25 comprises a second part 30 and two first parts 35. The neutralizing agent 25 is confined within an enclosed cavity 50 defined by the first parts 35 and the second part 30. In this way of confining the neutralizing agent 25, the neutralizing agent 25 can have any suitable form such as liquid, solid, particle, porous, concentrated, powder, pill, pellet or even gas. In case the neutralizing agent is a fluid, a coating of the inner surface is needed. If such a coating is not provided, the second part 30 will change its dimension caused by absorbtion of the neutralizing fluid in the second part 30.

The size of the container means 20 should be large enough for containing an amount of the neutralizing agent 25, that is, in the case of utilizing catalase as a neutralizing agent, typically of an internal diameter of 5,5 mm and an internal height of 5 mm.

The diameter of the first parts 35 should be slightly larger than the internal diameter of the second part 30 when that part has not been exposed to the disinfection agent. This will enable a resiliency force applied to the edges of the first parts 35 holding the first parts 35 in the position shown in FIG. 3 prior to and in the beginning of the disinfection process.

The shape of the first parts 35 is actual not crucial for principle of the mode of operation of the container means 20 for holding a neutralizing agent. The first parts 35 of the embodiment shown in FIG. 3 have been given a 3-dimensional shape where the rim 40 of the first parts 35 is deflected relative to the bottom surface 45 of the first parts 35. The angle could be varied from 0° to 180° without destroying the principle of the mode of operation of the container means 20 for holding a neutralizing agent.

The first parts 35 can be made of any material which change dimension when exposed to a fluid, but in such cases the expansion coefficient of the material should be lower than the expansion coefficient for the material used for the second part 30. The first parts 35 could of course also be made of a material which does not change dimension at all when exposed to a fluid such as plastic, metal, glass, cellulose based material or polymer based material.

The container means 20 for holding a neutralizing agent could be manufactured to have nearly any total density at all. For instance, the container means 20 could be given a density lower than, similar to, or even higher than that of the disinfection fluid, whereby the vertical position of the container means 20 in the disinfection fluid can be predetermined.

Due to the shape of the second part 30, the internal diameter of that part will increase when the second part 30 absorbs disinfection fluid or any fluid which can be absorbed by the material of which the second part 30 is manufactured from. This is due to the fact that all of the material from which the second part 30 is made of will expand. In the first embodiment of the container means 20 the second part 30 is shown as being tubular shaped which, because expansion thereof when exposed to a fluid will increase the internal diameter of the second part 30.

Figure 4:
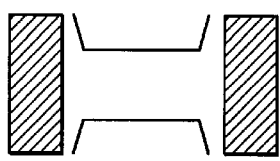
FIG. 4 shows an open state of the container means of FIG. 1, in the first embodiment.

Firstly, the use of the container means 20 holding the neutralizing agent 25 in the first embodiment will be discussed with reference to FIGS. 3–4. Later on, a similar discussion will be given with reference to the 5 other embodiments of the invention.

During the cleaning process, the container means 20 holding the neutralizing agent 25 is placed inside a container for receiving a contact lens and a disinfection fluid.

Once the contact lens and the container means 20 have been placed inside the container, disinfection fluid is poured into the container (or vice versa). When the disinfection fluid has been added, the second part 30 begins to absorb the disinfection fluid.

As the inner surface of the second part 30 is not exposed to the disinfection fluid or to any fluid at all, a transport process of fluid from the outer surface and from the end portion of the second part 30 towards that inner surface of the second part 30 takes place followed by an expansion of the elements of the second part 30 which has being wetted by the penetrating fluid.

Therefore, in the beginning of the cleaning process the expansion of the second part 30 will substantially occur in the outer parts of the second part 30 or the expansion rate will at least be slower than if the all of the surface of the second part 30 was exposed to the disinfection fluid or any fluid at all.

As a result of this, in combination with the fastening of the first parts 35 to the inner sides of the second part 30 due to the resiliency force applied to the edges of the first parts 35, is that the disinfection agent is not able to contact the neutralizing agent 25 in the beginning of the disinfection process, whereby the neutralizing of the disinfection fluid is postponed, leaving a high concentration of the disinfection fluid in a first period of the treatment process of the contact lenses.

The point in time when disinfection agent gets into contact with the neutralizing agent is, among other factors, controlled by the thickness of the second part and the diameter of the first parts 35 relative to the internal diameter of the second part 30.

Generally, when other things being equal except the thickness of the second part 30, the point in time when the disinfection agent is able contact the neutralizing agent 25 located in the substantially closed cavity 50 due to the creation of a communication passage as a result of the expansion of the second part 30 is related to the thickness of the second part 30.

When a communication passage is created in the container means 20 due to the expansion of the second part 30 and perhaps also the first parts 35, the neutralizing process is initiated.

Figure 5:
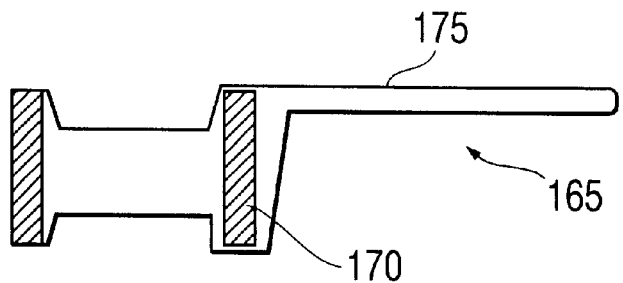
FIG. 5 is a cross sectional view of the container means in a second embodiment of the invention.

A second embodiment of the container means for holding a neutralizing agent according to the invention is shown in FIG. 5. In this embodiment a first part 165 covers the openings of the second part 170 in the way shown in FIG. 5. The straight part 175 of the first part 165 is intended to be used to handle the container means once the container means is placed in the container where the cleaning process is supposed to take place.

Figure 6:
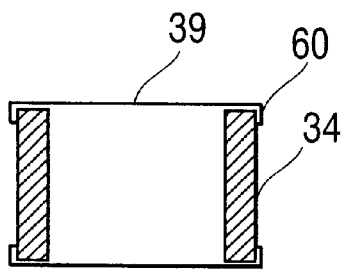
FIG. 6 is a cross sectional view of the container means in a third embodiment of the invention.

A third embodiment of the container means for holding a neutralizing agent according to the invention is shown in FIG. 6. In this embodiment, the first parts 39 extend beyond the second part 34. The first parts 39 have an edge 60 and the internal diameter of the first parts 39 is smaller than the outer diameter of the second part 34 when that element has not been exposed to any fluid. When the first parts 39 are placed on the top of the second part 34, a resiliency force due to a small compression of the second part and/or a deformation of the first parts 39 will keep the first parts 39 in a proper position.

When the container means for holding a neutralizing agent is exposed to the disinfection fluid, the second part 34 will begin to swell up. As the change of dimension of the first part 39 is lower than the change of dimension of the second part 34, the larger deformation of the second part 34 will create a force on the edge of the first parts 39 with a force component in the axial direction of the second part 34. This component will, when it becomes large enough, force the first parts 39 of the second part 34 away from the second part 34 leaving a communication passage for the disinfection fluid to enter the cavity containing the neutralizing agent.

The first parts 39 and the second part 34 could also be manufactured in such a way that the expansion coefficient of the first parts 39 is larger than the expansion coefficient of the second part 34. In this case, the internal diameter of the first parts 39 is larger than the external diameter of the second part 34 at the end of the expansion process whereby the first parts 39 are no longer fixed in position, thereby creating an internal communication passage.

Figure 7:
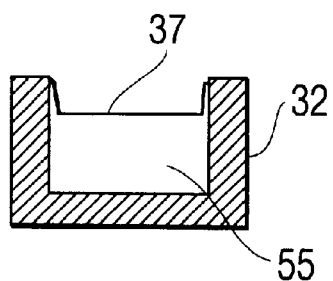
FIG. 7 is a cross sectional view of the container means in a fourth embodiment of the invention.
Figure 8:
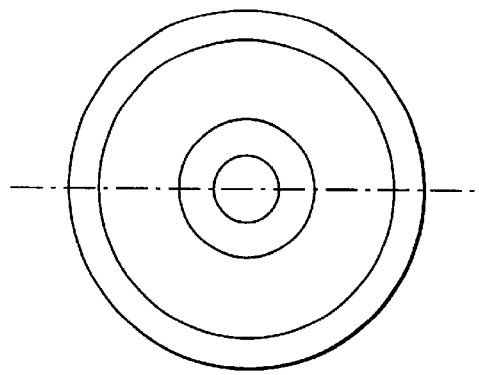
FIG. 8 is a top view of the container means for holding a disinfection agent and/or neutralizing agent in a fifth embodiment of the invention.

A fourth embodiment of the container means for holding a neutralizing agent according to the invention is shown in FIG. 7.

In this embodiment, the second part 32 defines a cavity 55 wherein the neutralizing agent 25 is placed. The cavity 55 is closed by a first part 37, similar to one of the first parts 35 used in the first embodiment of container means for holding a neutralizing agent.

The mode of operation of the fourth embodiment is similar to that of the first embodiment of the container means, i.e. as the second part 32 is exposed to a fluid, this part will swell up followed by an enlargement of the internal diameter of the second part 32. This enlargement will, if the expansion coefficient is larger for the second part 32 than for the one of the first part 37, create a communication passage enabling the fluid to get into contact with the disinfection substance inside the cavity 55.

It is, of course, possible to combine the features of the third and the fourth embodiment of the container means for holding a neutralizing agent in such a way that the first part 39 of the third embodiment is used instead of the shown first part 37 of the fourth embodiment or vice versa.

A fifth embodiment of the container means for holding a neutralizing agent according to the invention is shown in FIGS. 8–11. In this embodiment the container means for holding the neutralizing agent comprises a first part 65 and a second part 70 which both are shown as circular members, but actually the shape of the two parts is not crucial for the mode of operation of the fifth embodiment of the container means, and the two parts can be given any desired shape.

The first part 65 comprises two separating walls; an inner separating wall 80 and an outer separating wall 75. These two separating walls define two cavities; an inner cavity 85 and an outer cavity 90.

Like the first part 65, the second part 70 comprises two separating walls; an inner separating wall 95 and an outer separating wall 100. Upon assembly of the first part 65 and second part 70 in the manner shown in FIG. 9, two cavities are defined referred to as an inner cavity 110 and an outer cavity 120.

In this embodiment of the container means, a resilient engagement of the first and the second part is achieved by the abutment of the outer separating wall 100 of the second part 70 against the outer separating wall 75 of the first part 65 and of the inner separating wall 95 of the second part 70 against the inner separating wall 80 of the first part 65.

Figure 9:
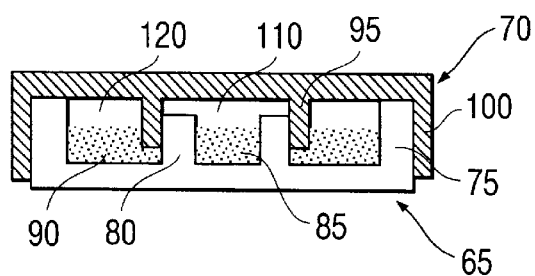
FIG. 9 is a cross sectional view of the container means of FIG. 8 along line I—I in the fifth embodiment of the invention.

It should be quite clear that the first part 65 and the second part 70 could be given any further separating walls than the two shown in the examples shown in FIG. 9, and it should also be clear that only one set of separating walls could be used, whereby only one cavity is defined, but in case two cavities 110 and 120 are defined, different substances usable in the disinfection process of the contact lenses could be contained in the cavities 110 and 120.

Also, in this embodiment of the container means, the first part 65 and the second part 70 can be made of materials which have different expansion coefficients when exposed to a fluid. Again it is assumed that the expansion coefficient is lower for the first part 65 than for the second part 70, and the first part could of course be made from a material which substantially does not change dimension when exposed to a fluid.

The outer diameter of the outer separating wall 75 is slightly larger than the inner diameter of the outer separating wall 100 and the outer diameter of the inner separating wall 80 is slightly larger than the inner diameter of the inner separating wall 95, whereby the first part 65 and the second part 70 are firmly joined.

Figure 10:
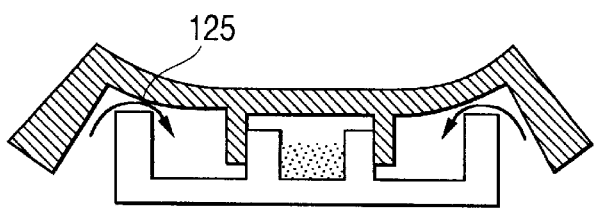
FIG. 10 shows a semi-open state of the container means of FIG. 8, in the fifth embodiment of the invention.
Figure 11:
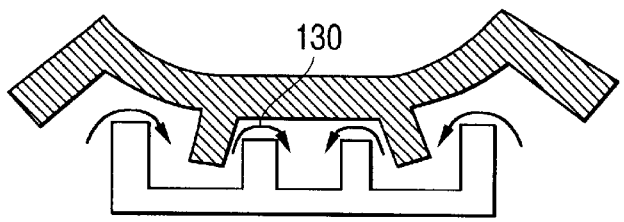
FIG. 11 shows an open state of the container means of FIG. 8, in the fifth embodiment of the invention.

The mode of use of the fifth embodiment of the container means is sketched in FIGS. 10–11. The container means for holding substances usable for the disinfection process is applied to a container (not shown) holding a fluid and the contact lenses (or other parts).

As shown in FIG. 10, the outer wall 100 of the second part 70 will, when fluid permeates into the top of the second part 100 and into the outer walls 100, be deflected outward leaving a communication passage 125 for the fluid to enter the outer cavity 120 whereby contact is initiated between the fluid and the substance located inside the outer cavity 120.

Due to the fact that the inner wall 95 of the second part 100 is exposed to fluid only after the communication passage 125 is formed by the outward deflection of the outer wall 100, substantially no deformation of the inner wall 95 takes place under the initial deformation process of the outer wall 100.

As the fluid enters the outer cavity 120, the inner wall 95 will start to swell up. The absorbtion of fluid in the inner wall 95 of the second part 70 is followed by a further deformation of the second part 70 as shown in FIG. 11 forming another communication passage 130 enabling the fluid to enter the inner cavity 110.

This is due to (as shown in FIGS. 10–11) the way the second part 70 deforms when it swell up.

As access to the outer cavity 120 and the inner cavity 110 is gained subsequently each other, a multiple cleansing process involving multiple substances that can not coexist is possible without any interference from the user of the cleaning apparatus.

In one example, the two cavities 110, 120 could contain two different enzymes needed in a cleaning and neutralizing process or the two cavities 110, 120 could contain a neutralizing agent and a substance e.g. salt changing the pH-value of the fluid, or the two cavities could contain a disinfection agent in the outer cavity 120 and a neutralizing agent in the inner cavity 110.

Figure 12:
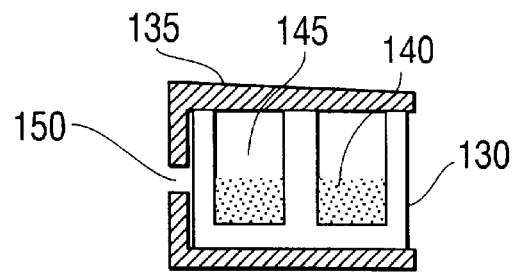
FIG. 12 is a cross sectional view of a container means for holding a disinfection agent and/or a neutralizing agent in a sixth embodiment of the invention.
Figure 13:
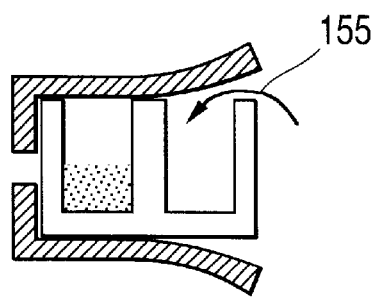
FIG. 13 shows a semi-open state of the container means of FIG. 12, in the sixth embodiment of the invention.
Figure 14:
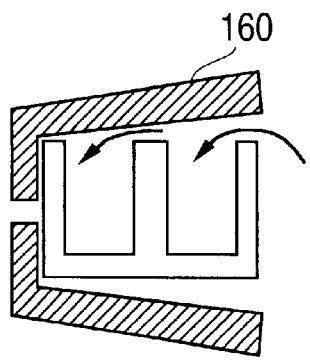
FIG. 14 shows an open state of the container means of FIG. 12, in the sixth embodiment of the invention.

A sixth embodiment of a container means according to the invention is shown in FIGS. 12–14. Again the container means comprises a first part 130 and a second part 135. Here, the first part 130 and the second part 135 in the embodiment are shown cylindrical. It should be quite clear that many other shapes of the first and the second parts 130, 135 are possible.

The first part 130 comprises two cavities 140 and 145. These cavities 140 and 145 can be given any desired form. Furthermore the volumes of the cavities 140 and 145 need not to be equal and can be made to match the amount of e.g. disinfection and neutralizing matters needed in a disinfection process. The first part 130 could of course comprise only one cavity 140 or three or more cavities.

The second part 135 of the embodiment is here shown as a hollow and open ended cylinder with a small opening 150 opposite the open end. The purpose of the small opening 150 is to ease the assembly of the container means. When the first part 130 is urged into the second part 135, air is pushed out through the small opening 150; otherwise a pressure would build up below at that end of the first part 130 which has been urged into the second part 135 rendering the assembly process of the first and the second parts 130, 135 difficult.

Again, the first part 130 and the second part 135 can be made from materials which change dimension when exposed to a fluid, and the rate of change of dimension of the material from which the part 130 is made from must be lower than the one of the second part 135 and can even be substantially zero.

Access to the cavities 140, 145 is gained in the following way:

The container means is situated in a container suitable for the disinfection process. The element to be disinfected is placed in the container suitable for the disinfection process. As the fluid contacts the outer surface of the second part 135, this part will swell up causing the open end of the second part 135 to deflect in the way shown in FIG. 13. By that deflection, a communication passage 155 is created whereby the fluid can enter the cavity 140.

At the same time, as the fluid enters the cavity 140, the internal surface of that part of the second part 135, which is deflected, is now exposed to the fluid whereby the deflection is increased after some time creating yet another communication passage 160.

As access to the outer cavity 120 and the inner cavity 110 is gained subsequent to each other, a multiple cleansing process, involving substances that can not coexist, is possible without any interference from the user of the cleaning apparatus.

In one example, the two cavities 110, 120 could contain two different enzymes needed in a cleaning and neutralizing process or the two cavities 110, 120 could contain a neutralizing agent and a substance e.g. salt, changing the pH-value of the fluid, or the two cavities could contain a disinfection agent in the outer cavity 120 and a neutralizing agent in the inner cavity 110.

Figure 15:
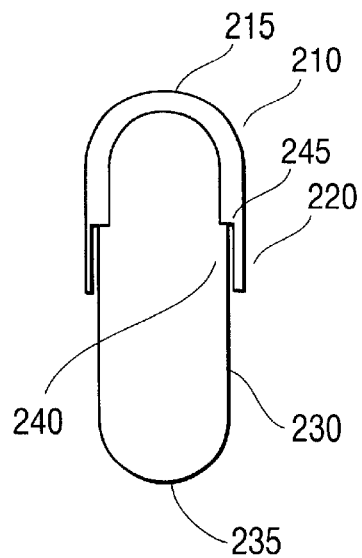
FIG. 15 is a cross sectional view of the container means in a seventh embodiment of the invention.

A seventh embodiment of the container means for holding a neutralising agent according to the invention is shown in FIG. 15. In this embodiment, a second part 210 covers the opening of a first part 230. The second part 210 is tubularly shaped having a rounded top part 215. Furthermore, the second part 210 has an engaging/abutment part 220 for use in engaging or abutting the second and the first parts 210, 230. In the embodiment shown in FIGS. 15 and 16, the thickness of the second part 210 is smaller along the engaging/abutment part 220.

The first part 230 is, as the fist part 210 tubularly shaped with a rounded bottom part, and the thickness of the first part 230 is kept constant. In FIG. 15 the engaging/abutment part 220 of the second part 210 is shown as a recess with straight sides, i.e. the wall of the recess has no projections.

As will follow from the description below, the formation of an opening in the eight embodiment of the container means does not depends on the above-described exact shape of the engaging part 220.

By shaping the engaging/abutment part 220 as a recess, the bottom of the recess 245 will act as means for positioning the second part in a correct, predetermined position relative to the first part, when the container means is assembled/combined. Other shapes of the second and the first parts 210, 230 will follow the same general principle (described below). One such other shape of the second part 210 could be a second part 210 with a substantially equal thickness distribution, eventually having a rectangular or square shaped cross section. Furthermore, the first part 230 could also be shaped to have a rectangular or square shaped cross section.

The seventh embodiment of a container means according to the invention could also be made to comprise two second parts 210. In such a case, the first part 230 would also be tubular shaped but be open ended in both ends. By applying two second parts 210, the container means would be less sensible to its orientation when placed in a cup-shaped container in the same way as described for the seventh embodiment of the container means.

Figure 16:
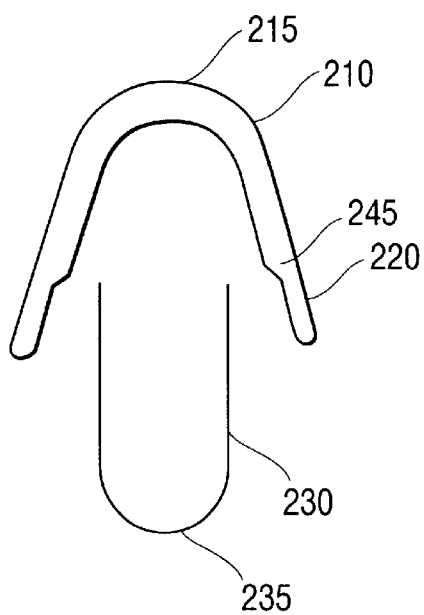
FIG. 16 shows an open state of the container means of FIG. 15, in the seventh embodiment of the invention.

Returning to the specific embodiment of the container means shown in FIGS. 15 and 16, normally the inner diameter of the second part 210 measured along the engaging/abutment part 220 is made smaller than the external diameter of the first part 230 measured at a contact area 240, i.e. the location where the engaging/abutment part 220 contacts the first part 230 when the container means is assembled/combined.

By assembling/combining the container means by a second part 210 having a smaller diameter than the first part 230, as described above, the two parts 210, 230 will be biased against each other when assembled/combined into a container.

In some situations, the engaging part 220 of the second part 210 comprises one or more projections, and the contact area 240 of the first part 230 comprises one or more corresponding cavities.

Such one or more projections together with the one or more corresponding cavities can guarantee a safer storage of the neutralising agent. If for instance the container means is stored in a vibrating environment, a simple biasing of the two parts 210, 230 may not be sufficient to keep the assembly/combination of the two parts together, but if the engaging part is provided with projections, a more safe storage is achieved.

It is emphasised that the one or more projections applied along the contact area 240 of the first part 230 and one or more corresponding cavities applied along the engaging part 220 of the second part 210 are equally well suited.

The projections could be triangularly shaped, rounded or any shape providing an engaging between the first and the second part 230, 210.

Again, the second part 210 is made of a material having a coefficient of expansion, when exposed to the fluid, being larger than the coefficient of expansion of the first part 230. Similar to the other embodiment of the container means according to the invention due to this difference in expansion coefficients, the second part 210 swells more than the first part 230

Furthermore, due to the rounded shape of the top part 215 of the second part 210 combined with the situation that only the exterior of the second and the first parts 210, 230 is wetted initially, when embedded in the disinfecting fluid, the expansion ensuing from the swelling of disinfecting fluid of the second part 210 and eventually the first part 230 is not geometrical linear, in the sense of linear blow up, as is indicated in FIG. 16.

In FIG. 16, the seventh embodiment of the container means according to the invention is shown in an open state. This state is reached after the second part 210 has expanded due to swelling of the fluid. As indicated on FIG. 16 an opening is formed providing access for the fluid to the neutralising substance located inside the cavity of the first part 230.

Figure 17:
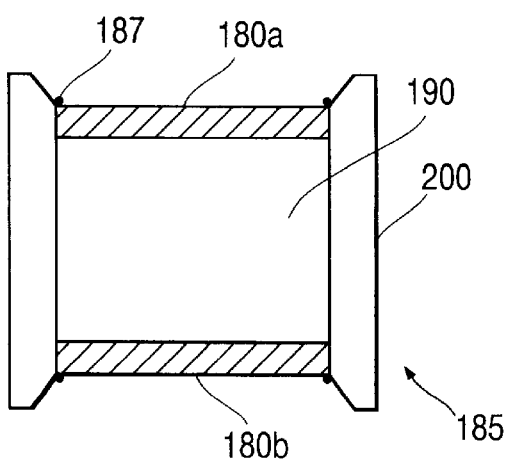
FIG. 17 is a cross sectional view of the container means in an eighth embodiment of the invention.

Referring to FIG. 17, an eighth embodiment of the container means used for holding the neutralising agent inside a cavity 190 is shown. In this embodiment, the container means is constituted by two second parts 180a,b and one first part 200. In this embodiment of the invention, the second parts 180a,b are formed of a material expanding when in contact with the disinfecting fluid, and the first part is formed of a material not expanding when in contact with the disinfecting fluid.

Also in this embodiment of the invention although preferred, it is not crucial for the basic principle of the invention to form the first part of a material not expanding when in contact with the disinfecting fluid. The opening of the container means would be achieved as long as the expansion coefficient of the second parts is greater than the expansion coefficient of the first parts.

The use of the eight embodiment of the invention will now be described in greater detail. The lenses, the cleaning fluid, and the container means are placed in a suitable receptacle for the cleaning and neutralising process, such as a cup-shaped receptacle. As the outer surface of the container means 185 is exposed to the cleaning fluid the second parts 180a,b will start to absorb the fluid.

If the introduction of the container means 185 ended up in a position in the cup-shaped receptacle whith one of the second parts, say 180a, in the vicinity of the wall parts of the cup-shaped receptacle, a gas bubble could be trapped between the wall part of the cup-shaped receptacle and the second part 180a. This situation will stop the absorption of cleaning fluid of the second part 180a, and if the container means 185 according to this embodiment of the invention was constituted by only one second part 180 no acces to the netralising agent would be provided for the cleaning fluid.

Furthermore, this situation would also occur in the case where the only second part ended up in a situation abutting a wall part of the cup-shaped receptacle. One such situation could be when a container means having only one second part was positioned up side down in the sense of the only second part being in contact with the bottom of the cup-shaped receptacle.

Therefore, two or more distinctive outer surface of the container means in the seventh embodiment of the invention is constituted by two second parts 180a,b. In this way it is practically impossible for the container means to be situated in the cup-shaped container in a manner where both second parts 180a,b are hindered from contacting the cleaning fluid.

As the second part 180 absorbs the disinfecting fluid, the second part expands and because the first part 180 does not expand as much as the second part 180, a bending of the second part 180 takes place providing a convex shape to the second part 180 as seen in FIG. 17.

At an instant which can be controlled by the thickness of the second parts 180a,b, at least one of the second parts 180a,b springs away from the container means, or an opening is formed in the container means if the second parts 180a,b are still be maintained in the first part 200. In the case where the at least one of the second parts 180a,b springs away from the container means, the cleaning fluid has an un-restricted passage to the neutralising agent, and the fluid will rapidly react with the neutralizing agent whereby the neutraling process is initiated.

In the case where an opening is formed, the cleaning fluid has an restricted passage to the neutralising agent but this will not prevent the reaction between the fluid and the neutralising agent. In this case, a gas bubble is created by the effect of the reaction and such a bubble will push away the second part 180.

Furthermore, the eighth embodiment of the container means according to the invention may comprises beads 187 as shown on FIG. 17. Such beads 187 will prevent the second part 180 from unintentional by leaving the first part 200 and the beads may also serve the purpose of controlling the leaving process of the second part 180.

Figure 18:
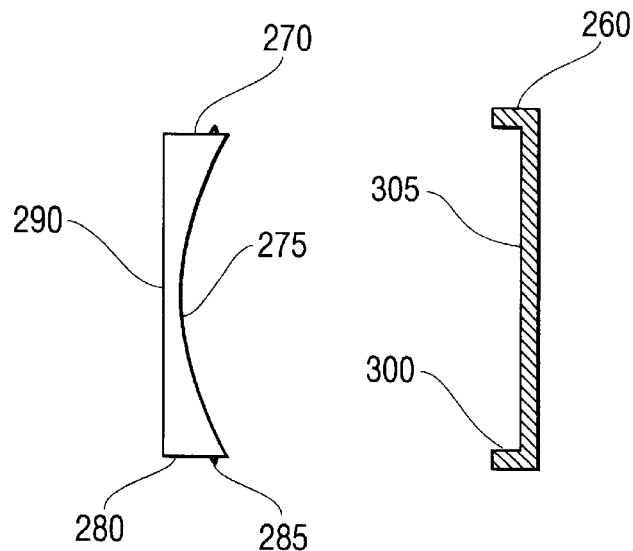
FIG. 18 is a cross sectional view of the container means in a ninth embodiment of the invention, the container means is shown in a pre-assembled/precombined state.
Figure 19:
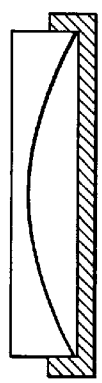
FIG. 19 is a cross sectional view of the container means of FIG. 18 shown in an assembled/combined state.
Figure 20:
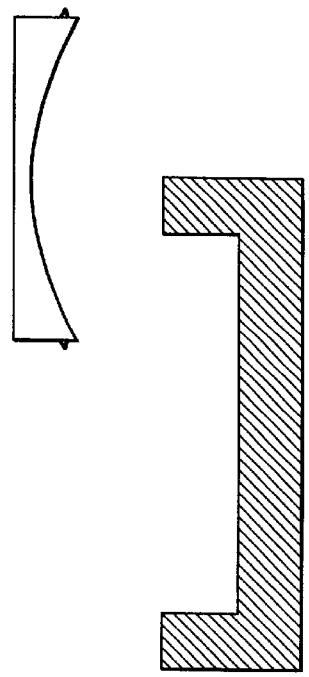
FIG. 20 is a cross sectional view of the container means of FIGS. 18 and 19 shown in an opened state.

A ninth embodiment of the container means for holding a neutralising agent according to the invention is shown in FIGS. 18–20. In this embodiment the container means is assembled/combined by a circular second part 260 and a circular first part 270.

The first part 270 comprises an interior convex part 275, a side part 280 having a projection 285 and a flat part 290. The second part 260 is also disc shaped with a basin 305 and serves as a lid closing the convex part 275 of the first part 270 thereby defining a sealed cavity for holding a substance used in the disinfecting process when the two parts 270, 260 are combined/assembled into the container means.

In this embodiment, the second part 260 is made of a material having a coefficient of expansion, when exposed to the fluid, being larger than the coefficient of expansion of the first part 270. Similar to other embodiments of the container means according to the invention, the second part 260 swells more than the first part 270 due to this difference in expansion coefficients. Furthermore, the first part could be made of a material having a coefficient of expansion of zero; i.e. the part will not swell.

Also in this embodiment of the invention, the internal diameter of the second part 260 is slightly smaller than the external diameter of the first part 270. By forming the two parts 260, 270 with different diameters, the two parts 260, 270 will be biased against each other when the container means is assembled/combined. This biasing of the two parts 260, 270 can retain them in a predetermined position relative to each other.

In order to secure the two parts 260, 270 in a predetermined position relative to each other, a projection 285 is provided on the side part 280 of the first part 270. A cavity 300 corresponding to the projection 285 is provided in the sidewall defining the basin 305. Upon assembly/combination of the two parts 260, 270 into the container means the two parts will engage with each other by means of the projection and cavity, whereby the second part 260 will be secured to the first part 290. Such a security is appreciated when the container means is exposed to for instance a rough handling occurring during transportation.

The ninth embodiment of the container means is preferably maintained in a predetermined orientation during cleaning of contact lenses and the subsequent neutralising of the cleaning substance. This preferred predetermined orientation of the container means is the orientation where the action of the gravity acts in the direction substantially parallel to the surface of the flat part 290 i.e. the orientation of gravity will with reference to FIGS. 18–20 be from the top of the figure to the bottom of the figure.

By orienting the container means relative to the orientation of the gravity as described above two valuable features are achieved. Firstly, the gravity will drag the second part away from convex part 275 when the second part 260 has swelled leaving unhindered access to the neutralising substance located therein. Secondly, since it in some cases are preferred to use a powdered neutralising agent, this powder will fall out of the convex part 275 after gravity has dragged the second part 260 away from the first part 270. These two features will prevent the access for the fluid to the neutralizing agent to be blocked.

Such a blocking could occur for instance if the container means was oriented with the gravity acting normal to the surface of the flat part 290. The blocking could be in the form of the second part 260 if this part does not change its position relative to the first part 270 but only swells. This situation could occur if no disinfecting fluid comes in contact with the neutralising agent inside the container means after the second part 260 has swelled.

On the other hand, this situation could also occur even if disinfecting fluid has entered the cavity inside the container means after the second part 260 has swelled. When the disinfecting fluid enters the cavity inside the container a gas bubble could be generated which could be trapped by the second part 260 whereby the bubble is not able to escape the cavity. If such a bubble is trapped, no new disinfecting fluid can enter the cavity inside the container means and the neutralising process will stop.

It should be noted that this interruption of the neutralising process is not the most common situation, but if a fail safe system is the aim, it is preferred that the container means is orientated such that the earth gravity acts in the direction along the surface of the flat part 290 as described above.

By orientating the container means in its most preferred orientation, the following opening process will take place after the container means and disinfecting fluid is placed in for instance a cup-shaped container used for disinfecting of lenses. Immediately after contact with the disinfecting fluid the second part 260 starts to swell whereby the internal diameter of the second part 260 will increase. When the internal diameter has increased a gap will be formed between the second and the first parts 260, 270 whereby the disinfecting fluid gets in contact with the neutralising agent through this gap. As the disinfecting fluid reacts with the neutralising agent, gas will be created and this gas will push on the bottom part of the basin 305 whereby the second part will be displaced relative to the first part 270. When the second part is displaced so much that is does no longer rest on the side part 280 of the first part 270 gravity will drag it away leaving free access for the disinfecting fluid to the neutralising agent.

As indicated on FIGS. 18–20 the ninth embodiment of the container means has a quite small aspect ratio, i.e. the ratio of the thickness and the diameter of the container means is quite small. The small aspect ratio will help to minimise the risk of a gas bubble sticking to the container means. If, on the other hand, the container means was provided with a very large aspect ratio, the laid open surface of the neutralising agent after the second part 305 has swelled will intensify the risk of a gas bubble sticking to the laid open surface of the neutralising agent and thereby interrupt the neutralising process. Large aspect ratios will similarly intensify the risk of a gas bubble sticking to the surface of the second part 305, thereby interrupting the swelling process.

Figure 21:
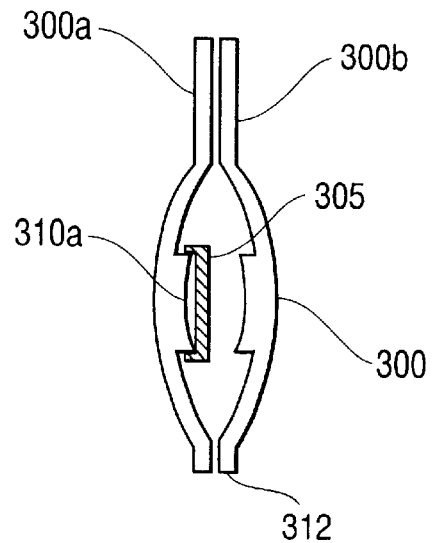
FIG. 21 is a cross sectional view of the ninth embodiment of the container means, the container means constituting af part of an orientation means.

In FIG. 21, the ninth embodiment of the container means according to the invention constitutes a part of an orientation means 300 for orientating the container means in a predetermined direction relative to a receptacle (not shown) used for the holding the lenses, the cleaning fluid and the container means during cleaning and subsequent neutralising. The second part of the container means is in FIG. 21 denoted 305 and the first part 310, respectively, 310a and 310b.

The orientation means 300 comprises two parts, 300a and 300b which in the figure is shown to be of similar shape, which is not necessarily preferred. In a preferred embodiment used for single use, the two parts cannot be separated.

In another embodiment, the two parts 300a,b are hingedly connected to each other by a hinge means 312, which preferably is an integral part of the container means 300. Such an integral part is in the embodiment shown in FIG. 21 provided by manufacturing the two orientation means 300 is a single piece in which the thickness of the material constituting the hinge means is made thinner than the rest of the retaining means 300 leaving the part of the retaining means 300 more flexible than the rest of the retaining means 300.

Furthermore, the two parts are maintained in the position relative to each other, shown in FIG. 21, by engaging means (not shown). The engaging means is for instance a hook connected to part 300a engaging with a corresponding part on part 300b.

The outer surface of the two parts 300a,b is porous such that the cleaning fluid can get into contact with the second part 305. Many choices of porous surfaces are available, but in the ninth embodiment of container means this porosity is provided by slits in the outer surfaces of the parts 300a,b.

Figure 22:
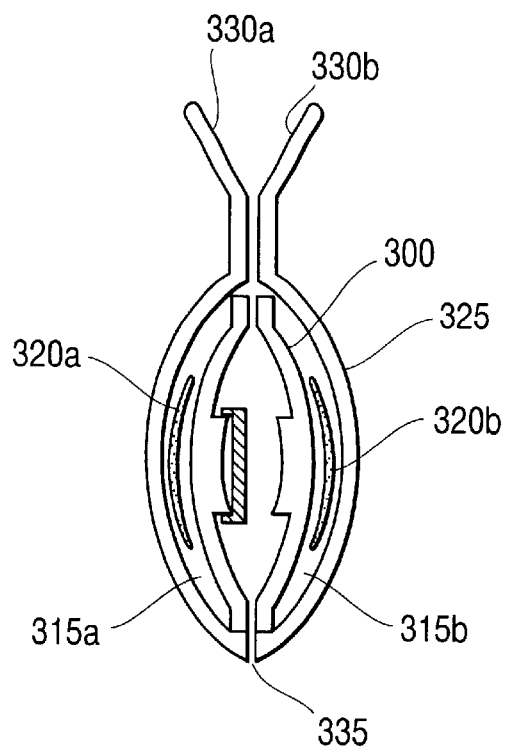
FIG. 22 is a cross sectional view of the ninth embodiment of the container means being constituting constituting a part of an orientation means, the orientation means being part of an enclsosing means.

Placing the container means inside a orientation means in the way shown in FIG. 22 provides another very important aspect of the container means according to the invention. As described above, the second part 305 swells up and is dragged away from the first part 310a by the gravity. As the second part 305 is not able to escape the orientation means 300 the risk that a user by a mistake takes the second part as a contact lens and introduces this second part 305 into his eye is eliminated. Such a confinement of the second part 305 also limits the degree of swelling of the second part. Such a limitation is appreciated in cases where the second part 305 is made of a material expanding a lot whereby the second part could end up taking up a large amount of the volume in the receptacle which is used in the cleaning process as described above.

A further manner of reducing eliminating this risk is to colouring the second and eventually also the first part with a colour rendering it easy for the user to distinguish the parts from the lenses. The colouring of the parts could of course also be applied to the other embodiments of the invention.

As shown in FIG. 21, two first parts 310a,b are provided in the orientation means 300 such that two containers means are available, if the other first part is provided with a second part. The use of two container means is advantageous in cases where two different substances are desired to be released and where such two substances not can be stored in contact with each other due to e.g. chemical reactions between them, or if the two substances are desired to be released at two different points in time. The last situation can be achieved by providing the second parts with different thickness and is e.g. useful, if the disinfecting/cleaning fluid is generated by a substance kept in one of the container means and the subsequent neutralising process is by the account of the substance kept in the other container means.

In FIG. 22, the orientation means 300 is enclosed in an enclosing means 325. As this enclosing means has an inner surface with a different radius of curvature than the outer surface of the retaining means 300 the enclosing provides receptacles 315a,b for receiving and holding the lenses 320a,b to be cleaned.

By placing the lenses close to the container means, a high concentration of the substance kept in the container in the fluid close to the lenses whereby a very efficient neutralising process is provided, or if the substance kept in the container means is a substance used for generating the cleaning/ disinfecting fluid a very efficient cleaning process is achieved. Furthermore, if two container means holding respectively a cleaning fluid generating substance and neutralising substance are provided, both processes will be very efficient.

The two parts 330a,b of the enclosing means 325 are hingedly connected to each other and retained in the relative position to each other by a hinge means 335 as described above for the orientation means 300, whereby access to receptacles is provided by pulling to two parts 330a,b away from each other. Furthermore, the two parts of the orientation means 300a,b can be made integral parts of the two parts 330a,b respectively.

The enclosing means 325 is similar to the orientation means 300 made porous by slits provided in the outer surface of the enclosing means. In this manner the cleaning fluid has an un-restricted access to both the contact lenses to be used and to the second part 305 of the container means for holding a substance used for neutralising the cleaning fluid.

The combination of container means, orientation means 300 and enclosing means 325 into a single unit makes the use of such a unit very simple. Furthermore, the shape of the parts constituting such a unit are easily handled by ordinary plastic moulding process such as blow moulding and due to the fact that the production price for such a unit is very low when large amounts are manufactured the unit can be disposed after use avoiding the demand for cleaning the container means after use.

The orientation means and/or the enclosing means can furthermore be provided with engaging means coorperating with with a receptacle used for cleaning the contact lenses. By use of such engaging means the orientation means and/or the enclosing means can be retained in a predetermined direction relative to vertical, such as described above, by retaining them relative to the rececptacle which in turn has a predetermined orientation.

These engaging means can be made such that the orientation means and/or the enclosing means can be placed therein before the cleaning process is initiated, or as in a case where the receptacle, the orientation means and the enclosing means is and integral unit, be a integral part of one or each of the means. In the first case the, engaging means could be a cavity having the shape of the bottom parts (the parts in the vicinity of the hinge means 312 or 335) of the orientation means or enclosing means respectively so as to make a close fit between the afore menthioned cavity and bottom parts.

What is claimed is:

1. A container which is suitable for holding at least one substance for use in a process for cleaning contact lenses using a fluid, the container comprising:
   at least one first and at least one second part assembled to form a sealed cavity for holding at least one substance, wherein the first part:
      is formed of a material having a first expansion coefficient when embedded in the fluid, and
      is at least substantially insoluble in the fluid,
   wherein the second part:
      is formed of a material having a second expansion coefficient when embedded in the fluid and
      is at least substantially insoluble in the fluid, and
      has an outer surface constituting a portion of an outer surface of the container, wherein:
   the first expansion coefficient is smaller than the second expansion coefficient, wherein:
      the container has at least one of:
         a) cross section wherein the first part defines an envelope curve and wherein at least one portion of the second part extends outside an envelope surface, and
         b) two or more portions of the outer surface of the assembled container are constituted by surface parts of the second part at at least two different sides thereof, and wherein:
      the materials of the first and the second parts are so that an initial, unexpanded sheet of the material of the second part will expand to a sheet of a mean thickness of at least 105% of the mean thickness of a fully expanded sheet of the material of the first part and of the same initial unexpanded thickness.

2. A container according to claim 1, wherein the dimensioning of the first and the second parts and the first and the second expansion coefficients are chosen so that, subsequent to the expansion of the first and/or the second parts, an opening is defined between first and second parts.

3. A container according to any of the claim 1, wherein the first part defines an open cavity and wherein the second part defines a cover at least substantially closing the cavity of the first part.

4. A container according to claim 3, wherein the second part abuts the first part along an inner or an outer surface part thereof.

5. A container according to claim 3, wherein the second part abuts the first part along an end surface part thereof.

6. A container according to claim 5, wherein the first and second parts are biased toward each other at the part of the end surface part.

7. A container according to claim 3, wherein the second part has a tubular part an outer edge portion of which is exposed to the fluid.

8. A container according to claim 7, wherein the first part is positioned so as to close the tubular part at the outer edge portion thereof.

9. A container according to claim 8, wherein the first part defines a plurality of open cavities, the second part defining a cover at least substantially closing the cavities of the first part.

10. A container according to claim 9, wherein the plurality of open cavities are positioned at least substantially concentrically and are separated by separating walls of the first part.

11. A container according to claim 10, wherein the tubular part encircles an outer cavity of the open cavities.

12. A container according to claim 11, wherein the first and second parts are biased toward each other at the separating walls of the first part and internal biasing means of the second part, the separating walls and the biasing means closing, at least in an unexpanded state, one of the cavities of the first part.

13. A container according to claim 9, wherein the plurality of open cavities are aligned side by side in the first part, the open cavities being separated by separating walls.

14. A container according to claim 13, wherein the tubular part is positioned so as to have an axis of symmetry along the aligned open cavities.

15. A container according to claim 8, wherein the outer edge portion is positioned at least substantially within a plane.

16. A container according to claim 8, wherein, at the outer edge portion, the second part has, compared to a main part of the second part, a larger proportion of the part of the surface thereof to be exposed to a fluid in relation to the volume of the material.

17. A container according to claim 1, wherein the first and second parts are biased toward each other.

18. A container according to claim 17, wherein the first and the second parts are shaped so as to be combined without the use of any separate fixing or combining means.

19. A container according to claim 1, wherein the first expansion coefficient is one where a sheet of the material of the first part having a thickness of 1 mm in an unexpanded condition will expanded to a mean thickness of 0.5–10 mm, when fully expanded in the fluid.

20. A container according claim 1, wherein the second expansion coefficient is one where a sheet of the material of the first part having a thickness of 1 mm in an unexpanded condition will expand to a mean thickness of 0.5–10 mm, when fully expanded in the fluid.

21. A container according to claim 20, wherein the material of the second part is so that an initial, unexpanded sheet of the material of the second part and of a predetermined thickness will expand to a sheet of a mean thickness of at least 110% to about 140% of the mean thickness of a fully expanded sheet of the material of the first material and of the same initial unexpanded thickness.

22. A container according to claim 20, wherein the first part is provided with means for facilitating deformation or breaking thereof at one or more predetermined points or along one or more predetermined lines.

23. A container according to claim 1, wherein the at least one part of the second part(s) extending outside the envelope surface has a part being convex.

24. A container according to claim 1, wherein the container further comprises orientation means for orientation of the container relative to the horizontal direction when positioned in a receptacle, the receptacle being adapted to hold the container, the contact lens, and the fluid when the contact lenses are cleaned.

25. A container according to claim 24, wherein the orientation means is adapted to orient the container with its axis of symmetry being substantially horizontal.

26. A container according to claim 24, wherein the orientation means further comprises enclosing means for enclosing the container.

27. A container according to claim 26, wherein the enclosing means comprise a porous fluid penetrable means adapted to allow the fluid to travel into the enclosing means and to prevent at least a major part of the expanded second part from escaping the enclosing means.

28. A container according to claim 27, wherein the orientation means further comprises means for holding the contact lenses during cleansing thereof.

29. A container according to claim 1, wherein the container is flat in a given direction when compared with an extension thereof in two directions which are perpendicular thereto and to each other.

30. A container according to claim 29, wherein the extension of the container along the given direction is at least 2 times smaller than the extension of the container along any one of the two directions.

31. A container according to claim 29, where the extension of the container in the given direction is less than 2 mm.

32. A container according to claim 31, wherein the first part defines a cavity having a bottom part and side parts and wherein the second part in the assembled container closes the cavity of the first part.

33. A container according to claim 32, wherein an internal height of the side parts from an internal surface part of the bottom part is less than 2 mm.

34. A container according to claim 33, wherein the container has an axis of symmetry directed at least substantially along the direction of the height of the side parts of the second part.

35. A container according to claim 34, wherein the second part defines a cavity, the cavity having a depth in the direction of the axis of symmetry, not exceeding 2 mm.

36. A container according to claim 34, wherein the second part defines a cavity, the cavity being shaped so that, when the axis of symmetry is at least substantially horizontal, no part of the inner surface of the cavity is horizontal.

37. A container containing at least one neutralising agent for neutralising a fluid during a contact lenses cleaning process using a fluid and/or at least one disinfecting and/or cleansing agent generating a disinfecting and/or cleansing fluid during a contact lenses cleaning process using a fluid, the container comprising:

at least one first and at least one second part assembled to form a sealed cavity for holding the at least one substance, wherein:
the first part is formed of a material having a first expansion coefficient when embedded in the fluid and is at least substantially insoluble in the fluid, wherein:
the second part is formed of a material having a second expansion coefficient when embedded in the fluid and is at least substantially insoluble in the fluid, the second part having an outer surface constituting a part of an outer surface of the container, wherein:
the first expansion coefficient is smaller than the second expansion coefficient, and wherein:
the container has at least one of:
a) a cross section wherein the first part defines an envelope curve and wherein at least one portion of the second part extends outside an envelope surface, and
b) two or more parts of the outer surface of the assembled container are constituted by surface portions of the second part at at least two different sides thereof, and at least one agent is contained in the sealed cavity.

38. A container according to claim 1, wherein the first expansion coefficient is one where a sheet of the material of the first part having a thickness of 1 mm in an unexpanded condition will expand to a mean thickness of 0.7–1.5 mm, when fully expanded in the fluid.

39. A container according to claim 1, wherein the first expansion coefficient is one where a sheet of the material of the first part having a thickness of 1 mm in an unexpanded condition will expand to a mean thickness of preferably 1.0 mm, when fully expanded in the fluid.

40. A container according to claim 1, wherein the second expansion coefficient is one where a sheet of the material of the first part having a thickness of 1 mm in an unexpanded condition will expand to a mean thickness of 1.2–5 mm, when fully expanded in the fluid.

41. A container according to claim 1, wherein the second expansion coefficient is one where a sheet of the material of the first part having a thickness of 1 mm in an unexpanded condition will expand to a mean thickness of 1.4 mm, when fully expanded in the fluid.

42. A container according to claim 29, wherein the extension of the container along the given direction is at least 3 times smaller than the extension of the container along any one of the two directions.

43. A container according to claim 29, wherein the extension of the container along the given direction is at least 4 times smaller than the extension of the container along any one of the two directions.

44. A container according to claim 29, wherein the extension of the container along the given direction is at least 5 times smaller than the extension of the container along any one of the two directions.

45. A container according to claim 29, wherein the extension of the container along the given direction is at least 6 times smaller than the extension of the container along any one of the two directions.

46. A container according to claim 29, wherein the extension of the container along the given direction is at least 6 times smaller than the extension of the container along any one of the two directions.

47. A container according to claim 29, wherein the extension of the container along the given direction is at least 10 times smaller than the extension of the container along any one of the two directions.

48. A container according to claim 29, wherein the extension of the container along the given direction is at least 20 times smaller than the extension of the container along any one of the two directions.

49. A container according to claim 29, wherein the extension of the container along the given direction is at least 30 times smaller than the extension of the container along any one of the two directions.

50. A container according to claim 29, wherein the extension of the container along the given direction is at least 50 times smaller than the extension of the container along any one of the two directions.

51. A container according to claim 29, wherein the extension of the container along the given direction is at least 70 times smaller than the extension of the container along any one of the two directions.

52. A container according to claim 29, wherein the extension of the container along the given direction is at least 85 times smaller than the extension of the container along any one of the two directions.

53. A container according to claim 29, wherein the extension of the container along the given direction is at least 100 times smaller than the extension of the container along any one of the two directions.

54. A container according to claim 29, where the extension of the container in the given direction is less than 1.5 mm.

55. A container according to claim 29, where the extension of the container in the given direction is less than 1 mm.

56. A container according to claim 29, where the extension of the container in the given direction is less than about 0.75 mm.

57. A container according to claim 29, where the extension of the container in the given direction is less than 0.5 mm.

58. A container according to claim 29, where the extension of the container in the given direction is less than 0.3 mm.

59. A container according to claim 32, wherein an internal height of the side parts from an internal surface part of the bottom part is less than 1.5 mm.

60. A container according to claim 32, wherein an internal height of the side parts from an internal surface part of the bottom part is less than 0.75 mm.

61. A container according to claim 32, wherein an internal height of the side parts from an internal surface part of the bottom part is less than 0.5 mm.

62. A container according to claim 32, wherein an internal height of the side parts from an internal surface part of the bottom part is less than 0.2 mm.

63. A container according to claim 34, wherein the second part defines a cavity, the cavity having a depth in the direction of the axis of symmetry, not exceeding 1.5 mm.

64. A container according to claim 34, wherein the second part defines a cavity, the cavity having a depth in the direction of the axis of symmetry, not exceeding 1 mm.

65. A container according to claim 34, wherein the second part defines a cavity, the cavity having a depth in the direction of the axis of symmetry, not exceeding 0.5 mm.

66. A container according to claim 34, wherein the second part defines a cavity, the cavity having a depth in the direction of the axis of symmetry, not exceeding 0.1 mm.

\* \* \* \* \*